United States Patent [19]

Anthony

[11] 4,324,068

[45] Apr. 13, 1982

[54] PRODUCTION OF ALGAE

[75] Inventor: Myron L. Anthony, Grand Junction, Colo.

[73] Assignee: Sax Zzyzx, Ltd., Clifton, Colo.

[21] Appl. No.: 126,844

[22] Filed: Mar. 3, 1980

[51] Int. Cl.³ .............................................. A01G 33/00
[52] U.S. Cl. .................................................... 47/1.4
[58] Field of Search ............................. 47/1.4, 65, 1.3

[56] References Cited

U.S. PATENT DOCUMENTS

| | | | |
|---|---|---|---|
| 2,715,795 | 8/1955 | Pallotta et al. | 47/1.4 X |
| 3,243,918 | 4/1966 | Machiedo | 47/1.4 |
| 3,959,923 | 6/1976 | Selke | 47/1.4 |
| 4,044,500 | 8/1977 | Hitzman | 47/1.4 |
| 4,065,875 | 1/1978 | Srna | 47/1.4 |
| 4,084,346 | 4/1978 | Stengel et al. | 47/1.4 |
| 4,163,342 | 8/1979 | Fogg et al. | 47/65 X |
| 4,209,943 | 7/1980 | Moeller et al. | 47/1.4 |

*Primary Examiner*—Robert E. Bagwill
*Attorney, Agent, or Firm*—Kinzer, Plyer, Dorn & McEachran

[57] ABSTRACT

Algae yield in a body of aqueous nutrient solution is increased by means of a nutrient thin-film surface culture substrate cycling between an illumination area and a non-illuminated refractory area in a closed system while feeding on the nutrient solution and CO₂. Illumination includes both light and/or electric ionic reduction.

9 Claims, 8 Drawing Figures

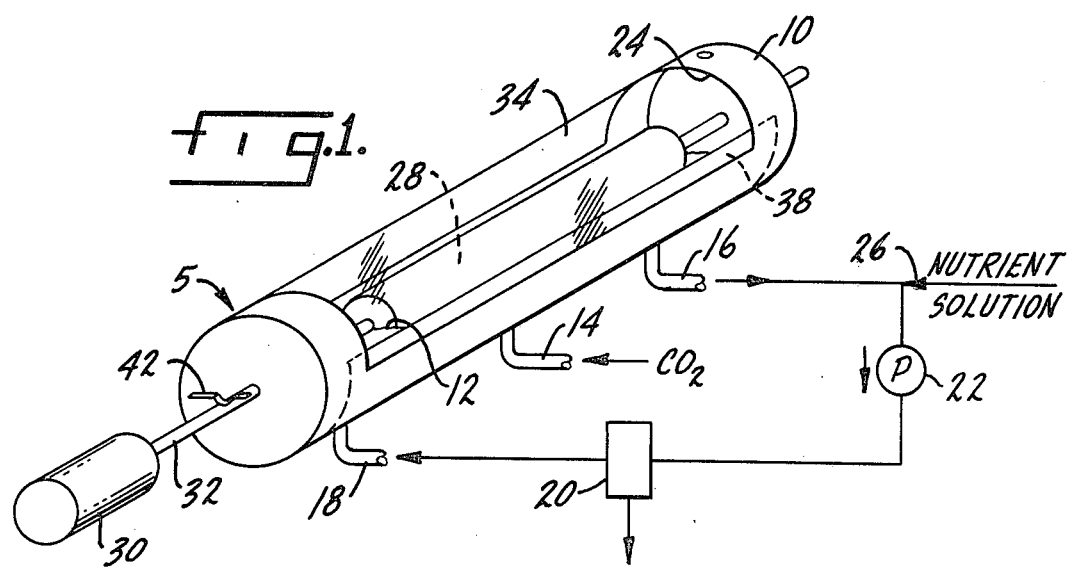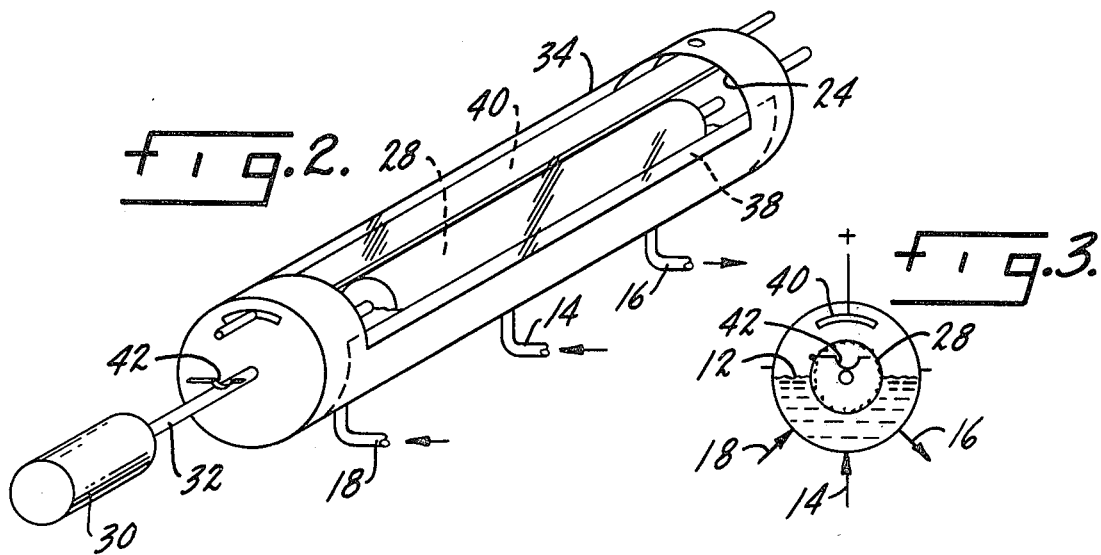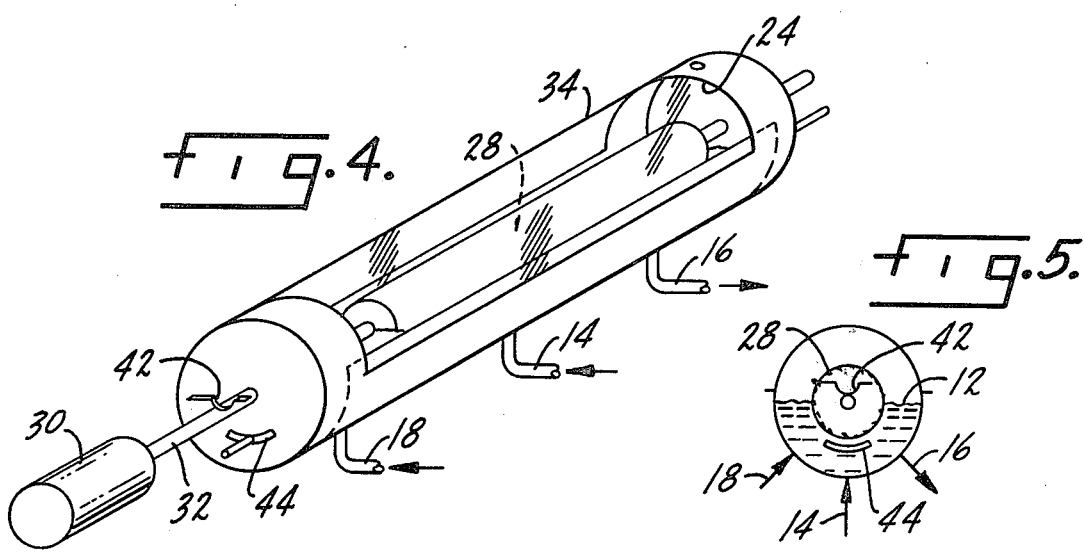

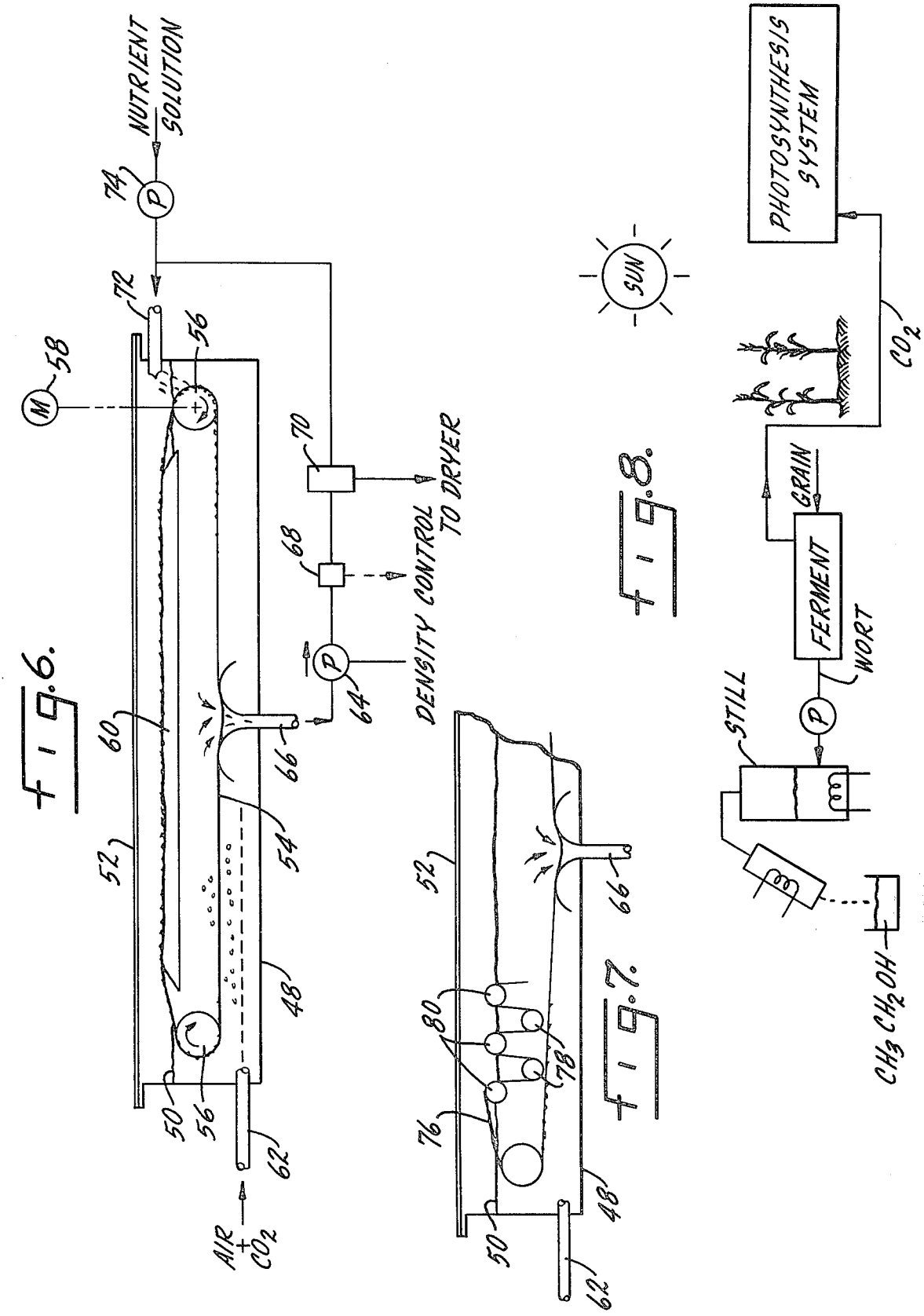

PRODUCTION OF ALGAE

This invention relates to growing of algae and harvesting the algae crop.

Algae is used as a food for mankind, especially in Japan, and it is also a source of fertilizer, agar and alginic acid to designate a few other uses of the material. Algae can be subjected to "pond culture" but ninety-five percent of the necessary photosynthesis takes place in the upper millimeter or so of the surface area of the pond so that a substantial harvest requires a large pond which can be quite expensive in the instance of an artificial pond.

The present invention achieves growth of algae at great savings in surface area and construction costs, to say nothing of making possible the growth of algae in areas where pond culture is not practical.

The present invention stems in part from my addressing the design of equipment for ethanol production, when I realized that nearly a pound and a half of dry algae can result from each pound of carbon dioxide which is generated as a waste product in the production of ethanol from the distillation of biomass such as grain wort, for example. Every pound of ethanol produced results in nearly a pound of $CO_2$.

The objects of the present invention are to avoid wasting carbon dioxide in the production of ethanol from grain wort or other fermentation processes, to find a substitute for "pond culture" of algae, to make possible the growth and reproduction of algae in apparatus which can be inexpensively manufactured and installed in minimum space and to operate that apparatus at high efficiency, ultimately separating algae deemed to be full grown from immature algae suspended in water.

BRIEF DESCRIPTION OF THE DRAWINGS

FIG. 1 is a schematic perspective view, partly diagrammatic, of apparatus constructed in accordance with the present invention;

FIG. 2 is a schematic perspective view, partly disgrammatic, of apparatus including electrical discharge means which may be incorporated for purposes of electrolysis in the apparatus of FIG. 1;

FIG. 3 is a diagrammatic end elevation view of the system of FIG. 2;

FIG. 4 is a perspective view, partly diagrammatic, of another alternate embodiment;

FIG. 5 is a diagrammatic end elevation view of the system of FIG. 4;

FIG. 6 is a side elevation view, partly diagrammatic, of still another alternate embodiment of the present invention;

FIG. 7 shows a variation of the embodiment of FIG. 6; and

FIG. 8 is a schematic view showing derivation and utilization of $CO_2$.

Photosynthesis by green plants and algae normally depends on sunlight and consumes water, as a source of the hydrogen used in reduction, and carbon dioxide, as the main acceptor for this hydrogen: See Photosynthesis, Second Edition, G. E. Fogg, 1972. Hence, by having carbon dioxide dissolved in water, together with the chemicals (nutrients and vitamins) required for algae growth and reproduction, "seed" algae suspended in the water and exposed to sunlight should grow and reproduce so that ultimately mature or full grown algae (at least deemed so) can be separated from immature algae which may be allowed to remain as the continuing seed source or inoculum. Indeed, pond cultures of algae are known in Japan, but these are invariably expensively constructed sites occupying a great deal of area and the yield is small per unit area of pond surface.

In the course of developing equipment for extracting ethanol from grain wort I recognized the great loss of carbon dioxide occurring from the process and this prompted me to ponder a useful application of the waste product. One embodiment of the emergent invention for growing algae while relying on the aforesaid source of carbon dioxide is illustrated generally as system 5 in FIG. 1. A closed cylindrical container 10 may be partially filled with water to level 12. The body of water contains a natural inoculum of algae in suspension, serving as the seed algae, and the body of water will also contain dissolved chemicals (vitamins and nutrients, such as phosphates and vitamin A) necessary to the healthy growth and reproduction of algae.

Carbon dioxide mixed with air may be introduced continuously into the body of water through inlet pipe 14 at a rate consistent with photosynthesis. Air is a source of nitrogen for life processes of the algae.

The body of water containing the dissolved materials and suspended algae will be circulated continuously between an outlet pipe 16 at one end of the container and the inlet 18 at the opposite end. The mixture in water will be delivered to a separator 20 (centrifuge) and constant recycling is made possible by a pump 22.

The container 10 is provided with a window opening 24 which defines the "daytime" (illumination) or sunlight area where photosynthesis is to take place. Inside the container a fine mesh drum 28 is supported for rotation, partly submerged in the body of water 12. The drum is rotated by a variable speed drive motor 30 and the necessary drive shaft 32.

Both the solution and algae in suspension (culture) will be entrained as a thin film by the mesh of the drum and as the latter rotates the entrained mixture in water will be rotated past the window area 24 (closed by a pane 34) allowing photosynthesis to occur. The algae grows by virtue of photosynthesis and reproduces itself so long as the chemicals (nutrients and vitamins) necessary for life support and regeneration processes are present in solution and in reasonable balance.

The separator 20 enables the mature (heavier) algae to be separated and thereby harvested, allowing the immature growth to remain behind as an inoculant allowing the process to continue.

It is strange, but nonetheless true, that photosynthesis involves a dark side or "refractory" time for photosynthesis dark reactions, and the present apparatus makes that possible in that the container inherently has a dark area (the contained body of water, especially the portion beneath the drum). It is also possible to construct the apparatus, FIG. 1, so that it will have an adjustable window shade denoted by reference character 38 which enables the effective window area to be selected; also, by having a variable speed drive motor the drum 28 may be accelerated or slowed, depending upon the best cycle times for exposure to the dark area and exposure to the daytime or illuminated area. In any event, it seems that the dark cycle or so-called refractory period is the period during which enzyme production and other life chemistry associated with photosynthesis takes place.

The necessary nutrient-vitamin solution is fed through inlet 26 and may be viewed as nothing more than a simulated sea water concentrate including light metal chlorides, heavy metal sulphates and the necessary vitamins essential to sea water algae cultures. Fresh water algae cultures require a fresh water nutrient solution.

The cycling from illumination area to dark area, by rotating the drum on which the water mixture is entrained or occluded, concerns the so-called doubling rate by which the algae "buds" are propagated or colonized, the number of cells or buds doubling in approximately two hours depending on the particular culture. If a normal culture or initial inoculum be taken modestly as ten million cells of algae per milliliter, the growth potential is enormous. Incidentally, one typical algae cell will have a diameter of approximately 0.004 inches and it may also be mentioned that the thin film phenomenon of the present invention (the thin film rotating with the drum) represents an effective surface area compared to a pond, the drum having many times the surface area of a pond. This comes about due to the repeated re-exposure of the drum or other algae film carrier compared to a generally stagnant pond surface. In other words, a cyclic film carrier utilizing rapid doubling algae is to be equated to at least ten or as much as a hundred times the equal area of pond water.

Even greater efficiency may be imparted to the process by subjecting the water solution to graded electrolysis, FIGS. 2 and 3, so that there is no need to depend upon the natural dissociation constant for water, which is quite low $10^{-14}$. Thus, hydrogen ions (H+) may be generated instantly across a photosyninsulated electrode 40 and a high tension ground slip ring 42 associated with the drum 28 which is conductive. The electrode 40 generates a high electric field across the thin-film algae bearing solution; about 10 KVDC per inch, or something on the order of 10 to 30 volts across a typical algae. A more rapid electrostatic field stress, if desired, may be produced by using rectified A.C., as shown in FIGS. 4 and 5. This embodiment utilizes an immersed exposed electrode 44, in this case the anode, wherein a form of electrolysis takes place to supply the reducing electron or hydrogen ion to mediate the photosynthesis (electrosynthesis) reaction. Alternating current in the range of 1–6 VAC is used.

An alternate embodiment of the system is shown in FIG. 6. A tank 48 is filled with the nutrient solution to level 50. The tank 48 has a window 52 on top allowing light to enter. A film carrier 54 in the form of an endless conveyor belt cycles the algae between illuminated and refractory periods. The carrier 54 is driven on pulleys 56 by a motor 58. A ramp 60 is provided to lift the carrier above the solution level 50 for the illuminated portion of the carrier run. An inlet 62 is provided for addition of air and carbon dioxide. The algae is harvested from the lower run of the film carrier 54 by a suction pump 64 operating through a collection pipe 66. The harvested algae is fed to a density controller 68 and then to a separator 70, which performs the same function as the separator 20 shown in FIG. 1. Immature algae is returned to the tank 48 through inlet pipe 72. A metering pump 74 adds fresh nutrient solution as needed, also through inlet pipe 72.

A still further embodiment is shown in FIG. 7. This is the same as the system of FIG. 6 except the fine mesh carrier 76 (which can be cloth or fiber glass) is cyclically immersed into the dark area followed by emergence to the light area accordion style by playing the belt alternately about idler rollers as 78 and 80.

The top of the tank represents the daytime area where light photosynthesis reactions take place and, again, this area may be variable by means of an adjustable or segmented shade; in like manner, the belt or screen 76 may be driven at variant speeds by means of a variable speed drive motor coupled to a drive sprocket by a drive shaft.

The idler rollers 78 may be immersed sufficiently that the dark time and area are inherent, and the lower pass of the belt also affords dark time. The adjustable shade may be employed to narrow or widen the illuminated area (enlarge or diminish illumination compared to dark) as in the foregoing embodiment. However, in most instances the cycle will be about fifty-fifty illumination/refractory times. It will be understood that the systems of either FIG. 6 or FIG. 7 could be equipped with electrodes to perform electrosynthesis as described above.

As noted above, conceptual aspects of the present invention were derived from a realization of the tremendous waste of carbon dioxide when generating wort as a source of ethanol from fermentation of grain, the ethanol of course to be used in gasohol mixtures. Thus as shown in FIG. 8, the grain or other biomass is allowed to ferment, resulting in a weak beer or wort which is pumped to a still in which the wort is concentrated to recover ethanol vapor which is condensed giving the desired liquid product. In the fermenting chamber, a great deal of carbon dioxide is generated and it is this source of carbon dioxide which will be delivered to the photosynthesis system in accordance with the present invention.

The embodiments of the invention in which an exclusive property or privilege is claimed are defined as follows:

1. Apparatus for growing and harvesting algae comprising:
   a container for holding a body of water containing an inoculum of algae in suspension and having both a window to admit light for photosynthesis into a space adjacent the body of water and a dark area for dark photosynthesis reaction;
   means to introduce carbon dioxide into the body of water to make a solution thereof in the presence of life-supporting chemicals for algae growth and reproduction; a fine mesh carrier inside the container and supported for cyclically presenting solution fractions containing algae in suspension to the window for photosynthesis and returning the fractions to the body of water;
   and means to remove the heavier algae from the body of water.

2. Apparatus according to claim 1 in which the fine mesh carrier is either of drum form or belt form.

3. Apparatus according to claim 1 or 2 including electrical discharge means to ionize the water to H+.

4. Apparatus according to claim 1 or 2 including means to allow the cycles to be variantly timed.

5. Apparatus according to claim 1 in which the inlet for carbon dioxide is attached to a chamber where fermentation generates carbon dioxide.

6. A method of growing and harvesting algae comprising: dissolving carbon dioxide in a body of water inside a container having a dark area for dark photosynthesis reaction, the body of water containing seed algae in suspension together with the chemicals required for algae growth and reproduction; continuously cycling samples of the solution containing the suspended seed algae back and forth between said dark time area and an area of daytime sunlight for photosynthesis; and selectively separating on the basis of weight from the body of water algae deemed full grown from immature algae the latter being allowed to remain behind for further growth.

7. A method according to claim 6 including the step of ionizing the body of water by electricity.

8. A method according to claim 6 or 7 including the step of preselecting the time for light or dark photosynthesis reactions.

9. A method according to claim 6 or 7 in which the cycling is accomplished by rotating the samples past a window illuminated with daylight and from thence back to the dark area.

* * * * *